United States Patent
Heethaar et al.

(10) Patent No.: US 6,339,722 B1
(45) Date of Patent: Jan. 15, 2002

(54) APPARATUS FOR THE IN-VIVO NON-INVASIVE MEASUREMENT OF A BIOLOGICAL PARAMETER CONCERNING A BODILY FLUID OF A PERSON OR ANIMAL

(75) Inventors: Robert Martin Heethaar, Cothen; Hendrik Gebhard Goovaerts, Kortenhoef, both of (NL)

(73) Assignee: A. J. van Liebergen Holding B.V. (NL)

( * ) Notice: Subject to any disclaimer, the term of this patent is extended or adjusted under 35 U.S.C. 154(b) by 0 days.

(21) Appl. No.: 09/043,864

(22) PCT Filed: Sep. 25, 1996

(86) PCT No.: PCT/NL96/00374

§ 371 Date: Jul. 13, 1998

§ 102(e) Date: Jul. 13, 1998

(87) PCT Pub. No.: WO97/11638

PCT Pub. Date: Apr. 3, 1997

(30) Foreign Application Priority Data

Sep. 26, 1995 (NL) ............................................. 1001282

(51) Int. Cl.$^7$ ................................................. A61B 5/05
(52) U.S. Cl. ....................................................... 600/547
(58) Field of Search ............................... 600/547, 481, 600/486, 500, 504, 506, 528, 546

(56) References Cited

U.S. PATENT DOCUMENTS

| 5,423,326 A | * | 6/1995 | Wang et al. | 128/713 |
| 5,685,316 A | * | 11/1997 | Schookin et al. | 128/713 |
| 5,807,272 A | * | 9/1998 | Kun et al. | 600/481 |

FOREIGN PATENT DOCUMENTS

| EP | 0 575 984 A2 | 12/1993 | ............ A61B/5/05 |
| WO | WO90/00367 | 1/1990 | ............ A61B/5/05 |

OTHER PUBLICATIONS

*Proceedings of the Annual International Conference of the IEEE Engineering in Medicine and Biology Society*, "Multiple Frequency system for body Composition Measurement," vol. 2, No. 2, Oct., 1993, pp. 1020–1021.

*Medical and Biological Engineering & Computing*, "Two–f-requency Impedance Plethysmograph: Real and Imaginary Parts," vol. 28, No. 1, Jan., 1990, pp. 38–42.

*Medical & Biological Engineering & Computing*, "Microprocessor–based system for Measurement of Electrical Imedances During Haemodialysis and in Postoperative Care," vol. 26, No. 1, Jan., 1988, pp. 75–80.

\* cited by examiner

*Primary Examiner*—Marvin M. Lateef
*Assistant Examiner*—Eleni Mantis Mercader
(74) *Attorney, Agent, or Firm*—D. Peter Hochberg; Katherine R. Vieyra; William H. Holt

(57) ABSTRACT

The invention relates to an apparatus for the in vivo non-invasive measurement of a biological parameter concerning a bodily fluid of a person or animal in accordance with a calculation model, wherein the apparatus is provided with connections for at least two pairs of electrodes (2–5, 8–11) to be placed on the skin of a part of the body, a pair of input electrodes (2, 3, 8, 9) for feeding a measuring alternating current to the part of the body and a measuring pair of electrodes (4, 5, 10, 11) for measuring the voltage at the measuring pair of electrodes, comprising a current source (7, 12) providing the measuring alternating current, a transformer (31) for the transformation of the measuring voltage into a bio-impedance signal, being a measure of the bio-impedance of the part of the body, and means for the generation of signals which form a measure for further parameters to be determined with the aid of the calculating model, said signals encompassing a signal forming a measure for the time derivative of the bio-impedance signal. The current source (7, 12) has a minimal radiation configuration and is suitable for generating a measuring current having a constant amplitude on at least two frequencies, a low frequency and a high frequency, in a frequency range of up to about 2000 kHz.

10 Claims, 7 Drawing Sheets

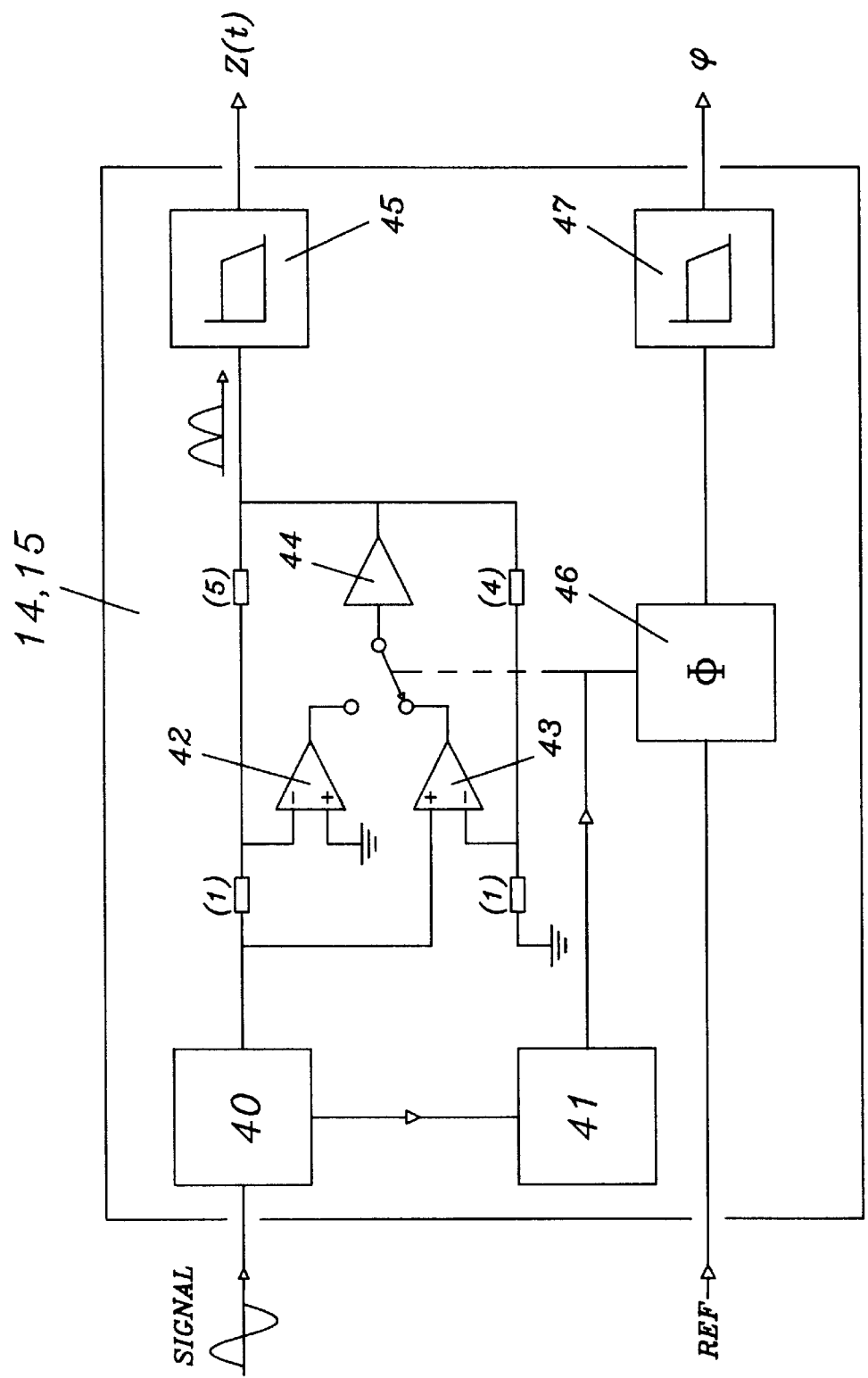

APPARATUS FOR THE IN-VIVO NON-INVASIVE MEASUREMENT OF A BIOLOGICAL PARAMETER CONCERNING A BODILY FLUID OF A PERSON OR ANIMAL

The present invention relates to an apparatus for the in-vivo non-invasive measurement of a biological parameter concerning a bodily fluid of a person or animal, wherein the apparatus is provided with at least two pairs of electrodes to be placed on the skin of a part of the body, a pair of input electrodes for feeding a measuring alternating current to the part of the body and a measuring pair of electrodes for measuring the voltage at the electrodes of the measuring pair of electrodes, comprising a current source providing the measuring alternating current, a converter for the transformation of the measuring voltage into a bio-impedance signal, being a measure of the bio-impedance of the part of the body, and means for the generation of signals which form a measure for further variables with the aid of which said parameter can be determined using the calculating model, said signals encompassing a signal forming a measure for the time derivative of the bio-impedance signal.

Such an apparatus is known from the international patent application WO-A-90/00367. This known apparatus is used to determine a number of biological parameters of the thorax of a patient by means of a bio-impedance measurement. However, the measurement is rather inaccurate because the fluid distribution in the patient is not taken into account. With the known apparatus there is also a local bio-impedance measurement; this is used for the determination of an average arterial pressure.

It is the object of the invention to apply the measuring results becoming available when employing this apparatus in such a way that the biological parameter can be determined more accurately.

To this end the apparatus of the invention is characterized in that the current source or current sources have an electrically symmetrical configuration and is provided with a galvanic separation in relation to the instrument earth and is suitable for generating a measuring current having a constant amplitude on at least two frequencies, a low frequency and a high frequency, in a frequency range of up to about 2000 kHz. This provides independent measurements and reduces interfering effects caused by electromagnetic radiation at high frequencies. It is noted that galvanic separation of the current sources is in itself known in the art; see for instance the article in Med. & Biol. Engineering & Computing, Vol. 28 (1990), January, No. 1, entitled: "Two-frequency impedance plethysmograph: real and imaginary parts". FIG. 2a of this application shows galvanic separation of the current sources and the measuring part of the instrument. The configuration employs thereto, however, three separate transformers to which large stray capacities attach which are detrimental for the accuracy of the instrument.

The biological parameters that can be determined by means of the apparatus according to the invention include preferably the measuring of a circulatory parameter and more preferably the stroke volume of a heart. Further, the so-called cardiac output which is derived from the stroke volume and the heart rhythm, the so-called cardiac index, the left ventricle ejection time, the right ventricle ejection time, the preejection period, the Heather index, the acceleration index, and venous occlusion plethysmography can also be determined by means of the apparatus. These terms are known to the expert and need no further explanation. Other biological parameters that may be determined by means of the apparatus are, for instance, the distribution between extracellular and intracellular bodily fluids and the distribution of fluid during a septic shock.

It is observed that the application of several frequencies for the determination of a biological parameter is known as such.

In the article "Multiple frequency system for body composition measurement", Proc. of the Int. Conf. of the IEEE Engineering in Medicine and Biology Society, Vol. 15, October 1993, pp. 1020, 1021, currents of different frequencies are used for the measurement and determination of a body parameter. The maximum frequency is, however, only 100 kHz, and no measures are given for combatting radiation problems. The publication is limited to the determination of changes in the bladder contents.

The article "Two-frequency impedance plethysmograph: real and imaginary parts", Med. & Biol. Engineering & Computing, 28 (1990) January, No. 1, pp. 38–42, describes a multi-frequency measuring system for the analysis of fluid volume ratios in the thorax where two different frequencies are used having a maximum measuring frequency of only 110 kHz.

The article "Microprocessor-based system for measurement of electrical impedance during haemodialysis and in postoperative care", Med. & Biol. Engineering & Computing, 26 (1988) January, No. 1, pp. 75–80, describes a system for tetrapolar impedance plethysmography for the determination of fluid and the fluid volume ratios in the thorax. Three oscillators are used for this purpose, two of which operate on 2½ and 100 kHz respectively and a third has an oscillation frequency of 1 kHz to 1 MHz.

The U.S. Pat. No. 4,870,578 describes an apparatus for the determination of the stroke volume of a heart by means of bio-impedance measurement. The apparatus according to this publication comprises means for sending a constant, high frequency current through the thorax of a person to be examined, as well as means for measuring a consequentially induced voltage over the thorax, from which signal the impedance of the particular thorax is derived. From this impedance the time derivative is determined, and a limited time portion of this time derivative subsequently serves as a measure for the stroke volume of the heart in the thorax.

U.S. Pat. No. 5,309,917 discusses a further development of such a bio-impedance measuring system departing from the known methods of determination according to Kubicek and Sramek.

According to Kubicek the stroke volume of the heart is determined by the formula $$SV = \rho \frac{L^2}{Z_0^2}\left(\frac{dZ}{dT}\right)_{min} \cdot VET$$

In this formula $\rho$ is the specific resistance of the blood, L is the distance at which the electrodes are placed for measuring the voltage, $Z_0$ is the average thorax resistance and VET is the ventricular ejection time. The current source provides a current having a frequency of about 100 kHz.

An alternative form according to which the stroke volume is determined is provided by Sramek:

$$SV = \frac{V_{EPT}}{Z_0} \cdot \left(VET\left(\frac{dZ}{dt}\right)\right)_{min}$$

in which $V_{EPT}$ is the volume of the thorax participating in the electric conduction. This volume depends on the height and weight of the particular person.

The general formula for the stroke volume may be expressed as $$SV = \mu \cdot \eta \frac{\left(VET\left(\frac{dZ}{dt}\right)\right)_{min}}{Z_0}$$

in which η is a personal form factor, and μ a corrective factor for oedema formation in the thorax.

According to U.S. Pat. No. 5,309,917 a time frequency diagram is determined for the measured time derivative of the bio-impedance signal. The stroke volume of the heart is then derived from this frequency diagram, while the stroke volume is assumed to be dependent on the time lapse between the first frequency signal in this distribution and the point in time when the time derivative of the bio-impedance signal reaches the maximum value.

Optimal separation of measurement results becoming available on the two different frequencies is obtained because the low frequency $f_l$ is in the region of about 1–64 kHz and the high frequency $f_h$ in the region of about 32–2000 kHz, such that in all cases $f_l$ is smaller than $f_h$. By choosing the measurement frequencies thus, the difference in sensitivity is optimal for both situations. The relatively low frequency currents are transmitted mainly through the extracellular fluid, while the high frequency currents are also transmitted through the intracellular fluid. Fluid distribution may, for instance, by analyzed by means of the so-called Cole-Cole-model, which is based on a Nyquist analysis of a simple equivalent-circuit diagram of the thorax, based on a parallel circuit of a purely resistive component for the relatively low frequencies and for the high frequencies a series connection of a resistive and a capacitive component. Consequently, by applying the known formulas for the determination of the stroke volume and other biological parameters, different frequencies provide independent measurements for those parameters. These measurements provide information about the above-mentioned correction factor μ. With the aid of the measured impedance $Z_0$, or through determination of the measured phase angle, ψ, the ratio intracellular and extracellular fluid can be determined at different frequencies.

Preferably the current source is suitable for simultaneous generation of the two frequencies. This has the advantage that the time the patient has to be connected to the apparatus for measurement is shortened.

In addition it is desirable that means are provided for the determination of maximum phase shift between the measuring current and the measuring voltage as a function of the frequency. This allows the electric transfer function of the particular part of the body to be determined, with the angular frequency being the independent variable. This permits at the same time the determination of the ratio between intracellular and extracellular fluid; because this ratio is directly related to the frequency at which the phase angle is at a maximum. With healthy test persons this maximum phase angle is at about 9 to 10° at 70 kHz. This corresponds to an intracellular/extracellular fluid ratio of 3:7. With septic patients the maximum phase angle is, for instance, between 3 and 6 °.

A preferred embodiment of the apparatus according to the invention is characterized in that said apparatus comprises four pairs of electrodes, two pairs of electrodes being intended for taking a transversal bio-impedance measurement and two pairs of electrodes being intended for taking a local bio-impedance measurement. In the case that the measurement is carried out on the thorax, the local bio-impedance measurement is to be carried out at a location removed from the heart.

The term "transversal measuring" used above, indicates a measurement in which the current runs substantially lengthways of the person to be examined.

The measure discussed just now allows a further correction to be carried out on the resulting measurements, due to the different test results of the cardiovascular system at a relatively low and a relatively high frequency. With a local bio-impedance measurement a measurement check is thus obtained in which the interfering influence of the cardiovascular system is eliminated. In this way the local measurement produces a correction signal to compensate the transversal measurement.

The apparatus is preferably provided with connecting means for connecting the current source and the transformer in series, in order to sequentially carry out the local bio-impedance measurement and the transversal bio-impedance measurement. This limits the number of components comprising the apparatus, and by always employing the same system parts an optimally reproducible measurement is obtained.

In another embodiment the apparatus according to the invention is characterized in that said apparatus comprises a current source or current sources suitable for the simultaneous generation of signals at two low frequencies and two high frequencies, so as to limit the inconvenience for a patient to be examined. These frequencies all range from about 4 to 2000 kHz, with a first low frequency and a first high frequency being coupled to a first two pairs of electrodes to carry out the local bio-impedance measurement and the second low frequency and the second high frequency being coupled to the second two pairs of electrodes to carry out the transversal bio-impedance measurement. In this way, both measurements can be carried out simultaneously.

It is further desirable that the measurement amplifier or measurement amplifiers are configured electrically symmetrical and are provided with a galvanic separation in relation to ground. This increases the resistance to common mode interference signals.

Also, the input stage of the apparatus is inductively coupled, thereby reducing transmission of the interference signal residue.

The invention will now be further elucidated with reference to the drawing, in which FIG. 1a represents schematically a first measuring arrangement of the apparatus according to the invention;

FIG. 6 shows an embodiment of the converters employed in the apparatus according to the invention.

Figure 1A:
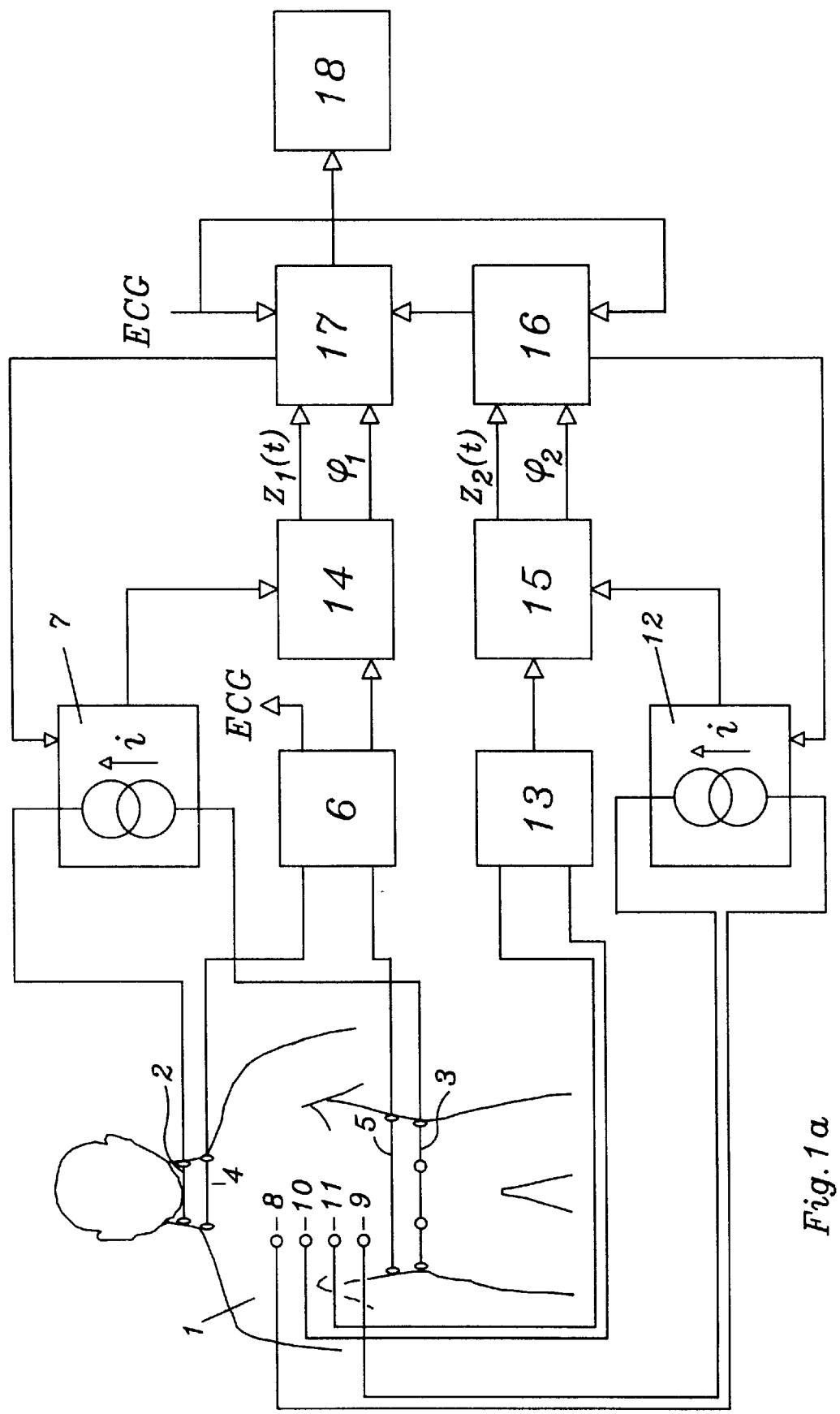
FIG. 1b represents schematically a second measuring arrangement of the apparatus according to the invention.

FIG. 1a shows a block diagram of an embodiment of the apparatus for carrying out simultaneous measurements on a patient 1. By means of current supply electrodes 2 and 3 current from a current source 7 is supplied to a patient 1. The voltage resulting from current passing through the tissue of the test person 1 is measured by means of a pair of electrodes 4 and 5 which are connected with a differential amplifier 6. The electrodes 4 and 5 serve for the transversal measurement. Current input electrodes 8 and 9 are locally placed on the patient 1 and are connected with current source 12. The resulting voltage over the tissue between said electrodes is measured by means of the electrodes 10 and 11 which are connected with differential amplifier 13. The electrodes 10 and 11 serve for the local measurement.

The output of the differential amplifier 6 is fed into a calculating element 14 providing an electric bio-impedance signal $Z_1(t)$ which is directly related to the bio-impedance of the thorax of the patient 1 as a function of the time and a phase signal $\psi_1$ which is directly related to the phase difference between the current supplied by means of a current source 7 and the voltage measured by electrodes 4 and 5. Similarly, the output of the differential amplifier 13 is supplied to the calculating element 15 which provides an electric bio-impedance signal $Z_2(t)$ which is directly related to the bio-impedance of a locally measured part of the body as a function of the time and a phase signal $\psi_2$ which is directly related to the phase difference between the current supplied into said part of the body and the resulting voltage over that part of the body as measured by means of the electrodes 10 and 11.

The electric bio-impedance signal $Z_1(t)$ and the phase signal $\psi_1$ are fed into a processor 17 in order to determine a parameter to be identified below. The frequency and possibly the amplitude of the current source 7 are preferably controlled by the processor 17. In order to carry out the necessary operations, the electrocardiogram (ECG) obtained at the output side of the differential amplifier 6 or from a separate ECG amplifier (not shown), is fed into the processor 17. Similarly, the signals $Z_2(t)$ and $\psi_2$ are fed into the processor 16 for the determination of the fluid distribution in the locally measured part of the body. The resulting parameters are then fed into the processor 17 for the determination of correction factors in the operations carried out by processor 17. The above-mentioned ECG also serves for the improvement of accuracy. The output of processor 17 showing the desired parameters, is connected to indicator 18 for display and registration purposes.

Figure 1B:
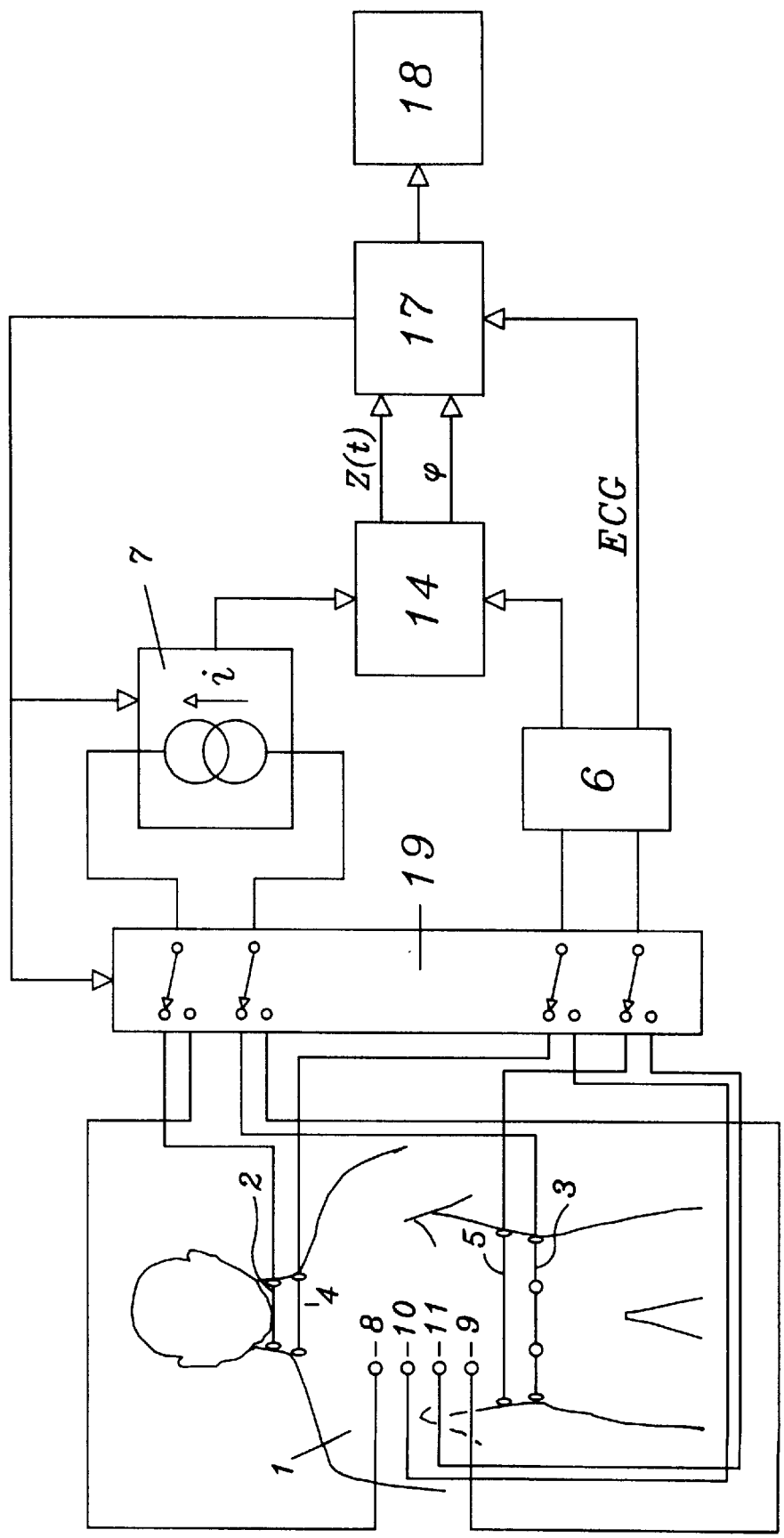

FIG. 1b shows the circuit suitable for sequential measurement on the patient 1. The functions of blocks 6, 7, 14, 17 and 18 have already been elucidated. The switch 19 is controlled by the processor 17 for carrying out sequential measuring on the thorax bio-impedance and measuring the local bio-impedance of a part of the body of patient 1. FIG. 1b shows clearly that in a first situation the current source 7 is connected with the electrodes 2 and 3, while the differential amplifier 6 is at the same time connected with the electrodes 4 and 5 by which measuring of the thorax bio-impedance can then take place. In the other situation said current source is connected with the electrodes 8 and 9, while said differential amplifier 6 is connected with the electrodes 10 and 11 so that local measuring of the bio-impedance of the part of the body of the patient 1 can take place.

Figure 2:
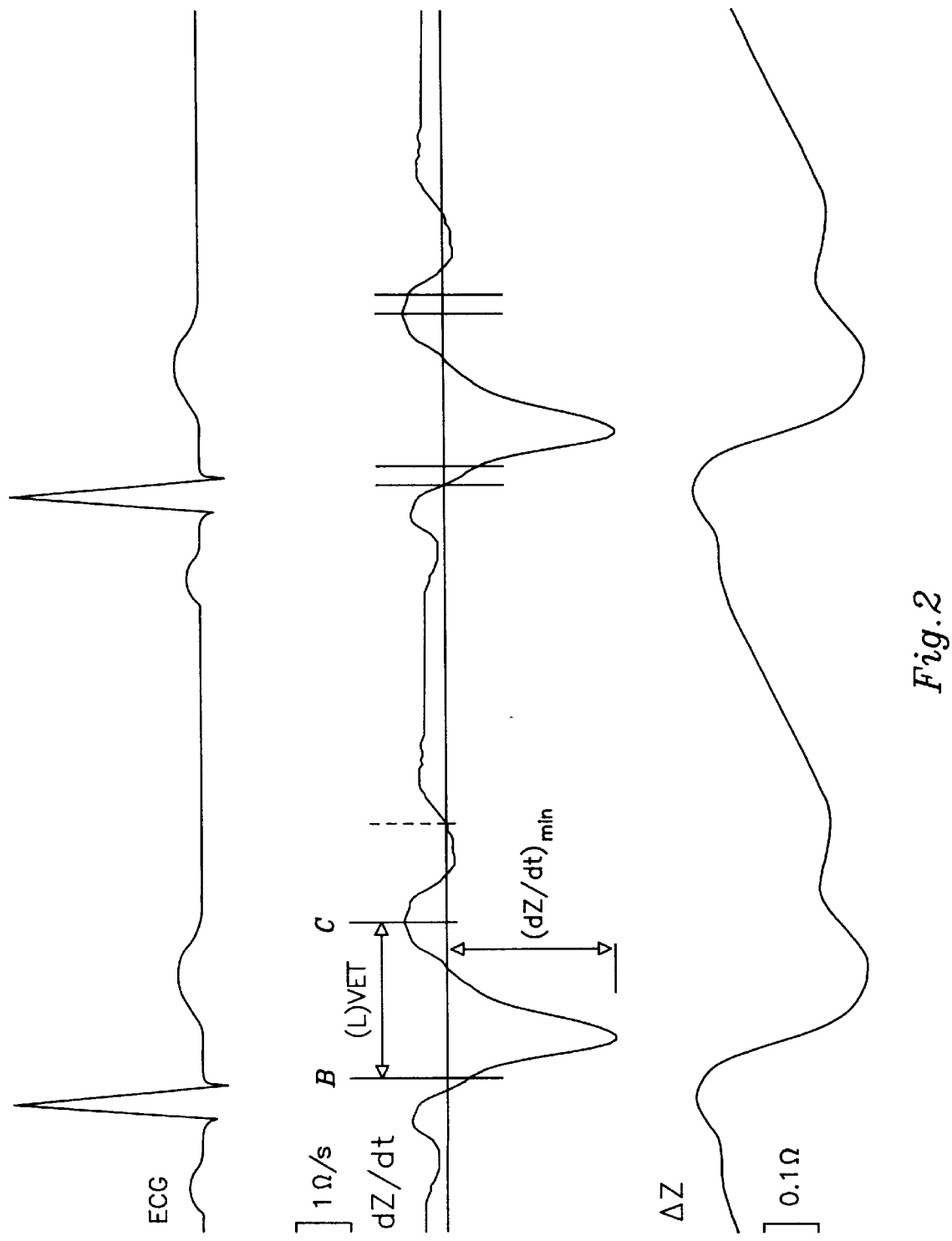
FIG. 2 shows an example of the progress of measuring signals perceived by the apparatus according to the invention.

FIG. 2 shows a typical progress of a bio-impedance signal $\Delta Z$, as measured with the differential amplifier 6 based on an excitation by current source 7. The progress of this signal is time-dependent in particular because of the pumping activity of the heart of the test person 1. The time derivative of the signal $\Delta Z$, $dZ/dt$, is shown one row higher in FIG. 2.

According to the prior art, when determining the stroke volume of the heart, this is approximated by multiplying the minimum value of the time derivative $(dZ/dt)_{min}$ by a time interval which is determined by the characteristic waveforms in the signal $dZ/dt$. In the field this time interval is indicated as (left) ventricular ejection time (abbreviated (L)VET), and is dependent on a point in time at the beginning of a curve indicated by B and a point in time determined by the next maximum in the time derivative indicated by C. For synchronization purposes the top row shows the electrocardiogram (ECG) of the test person 1.

In accordance with the invention, measuring errors ensuing due to over- or underweight of the test person 1 or due to measurements carried out under conditions where the normal moisture balance of the test person is upset, for instance with oedema formation, are prevented due to the fact that the current source 7 can generate and electric current having at least two frequencies. By processing the data from current source 7 in a calculating element 14, the measuring results becoming available from differential amplifier 6 are converted into a bio-impedance signal Z, while this element 14 also determines the phase difference $\psi$ between the current from source 7 and the voltage from amplifier 6. The current source 7 can generate a current having frequencies in the range of about 4 kHz to about 2000 kHz; if desired, the current source 7 can simultaneously generate currents having different frequencies. In a processor 17, the frequency-dependent measuring results for a particular thorax transfer model may be transformed into a current distribution factor which is dependent on the geometry of the test person 1. For this the moisture distribution according to the Cole-Cole-model may be used by means of which a current ratio between the intracellular fluid and the extracellular fluid can be determined. This current ratio corresponds to the current distribution over the cardiovascular system and the rest of the thorax. In a particular embodiment the current source 7 is suitable for the generation of a electric current having a frequency sweep of about 4 kHz to 2000 kHz, while the calculation element 14 is also suitable for the determination of the maximum phase angle dependent on the frequency. Based on this data the moisture distribution can be determined with the aid of a Bode analysis of the transfer model of the thorax by determining the maximum phase angle and possibly the frequency at which this occurs. Normally the maximum phase angle is about 9 to 10° at a frequency of 70 kHz.

Similarly, a local impedance measurement can be carried out by means of the electrode pairs 8, 9, and 10, 11. The measurement results becoming available through the measuring amplifier 13, together with data from the current source 12 are fed into a calculation element 15, and from these a local impedance value and the phase angle between the current from the source 12 and the voltage from the differential amplifier 13 are determined. In a manner similar to the one described above, the measuring data thus derived are further processed in a processor 16 in order to determine the current distribution over the cardiovascular system and the rest of the thorax. This measuring signal suffering no interference from the heart's pumping action, is subsequently also fed into the processor 17 to compensate the measuring data obtained from the transversal measurement. The measuring data thus corrected may then be made available for reading via an indicator 18. If necessary, special operations may be carried out by feeding the ECG signal to the processors 16, 17.

Figure 3:
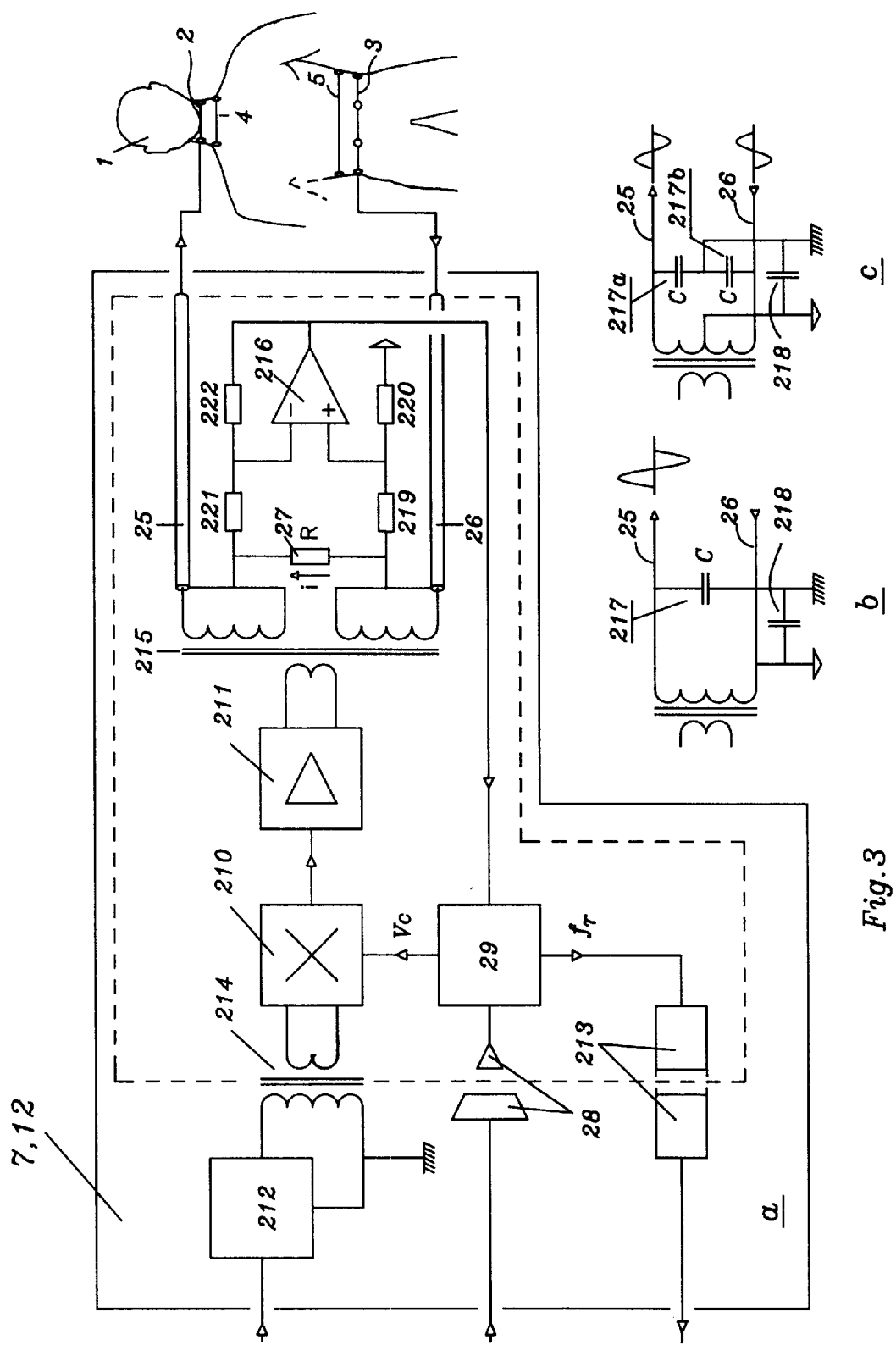
FIG. 3a represents schematically the current source of the apparatus according to the invention.
FIG. 3b represents schematically a non-low-radiation current source according to the prior art.
FIG. 3c represents schematically a low-radiation current source according to the invention.

FIG. 3a shows the block diagram of the current source. The current source comprises a floating part which is electrically insulated with respect to its housing. A pure sine form whose frequency is controlled by a processor 17 is generated by means of the oscillator 212 and is inductively coupled to the floating part of the current source by means of the transformer 214. The output of said transformer is fed into a wideband amplifier 210 whose amplification is controlled by the processor 29. The output of said amplifier is fed into a wideband capacity amplifier 211, being coupled at its output side via a transformer 215 to the current feed electrodes placed on the patient 1.

The transformer 215 comprises two analogous secondary windings connected with each other in such a way that a current i can be measured by means of determining the voltage over a precision resistor 27. The live cables 25 and 26 are protected in order to reduce the electromagnetic field generated by this cable. However, this protection could cause a problem, because with the increased frequency an increased current resulting from the capacity of these cables, plays a role. However, in the embodiment shown employing secondary windings of transformer 215 and precision resistor 27, only the current running through the patient is determined. The wideband amplifier 216 measures the voltage produced at the spot of said precision resistor 27, which data is fed into processor 29 in order to be compared with an amplitude control signal coming, for instance, from processor 17 or from a reference present in the processor 29. The processor 29 emits a voltage Vc for the control of the amplification of amplifier 210. By the control loop thus realized, the amplitude of current i is directly related to the amplitude control signal so that said current is stabilized. The amplitude control signal is preferably generated by processor 17. At the same time processor 29 transforms the voltage over resistor 27 into a reference signal $f_r$ for the phase measurement. By employing an optocoupler 213 this signal is transmitted galvanically separated.

As a rule, an electric apparatus is prone to the development of electromagnetic stray fields. The provision of a floating part which is electrically insulated from the rest of the electronics, reduces these stray fields to a certain extent.

FIG. 3b shows a current source according to the prior art, from which can be seen that the amplitude of the parasitic current is determined by the measure of parasitic capacitor 217 and the insulation capacitor 218. The parasitic capacitor 217 is determined by the body surface of the patient 1. The diagram in FIG. 3c shows the symmetric arrangement according to the invention, as a result of which no voltage is generated over the insulation capacitor with the result that the effective parasitic capacitor is reduced.

Figure 4:
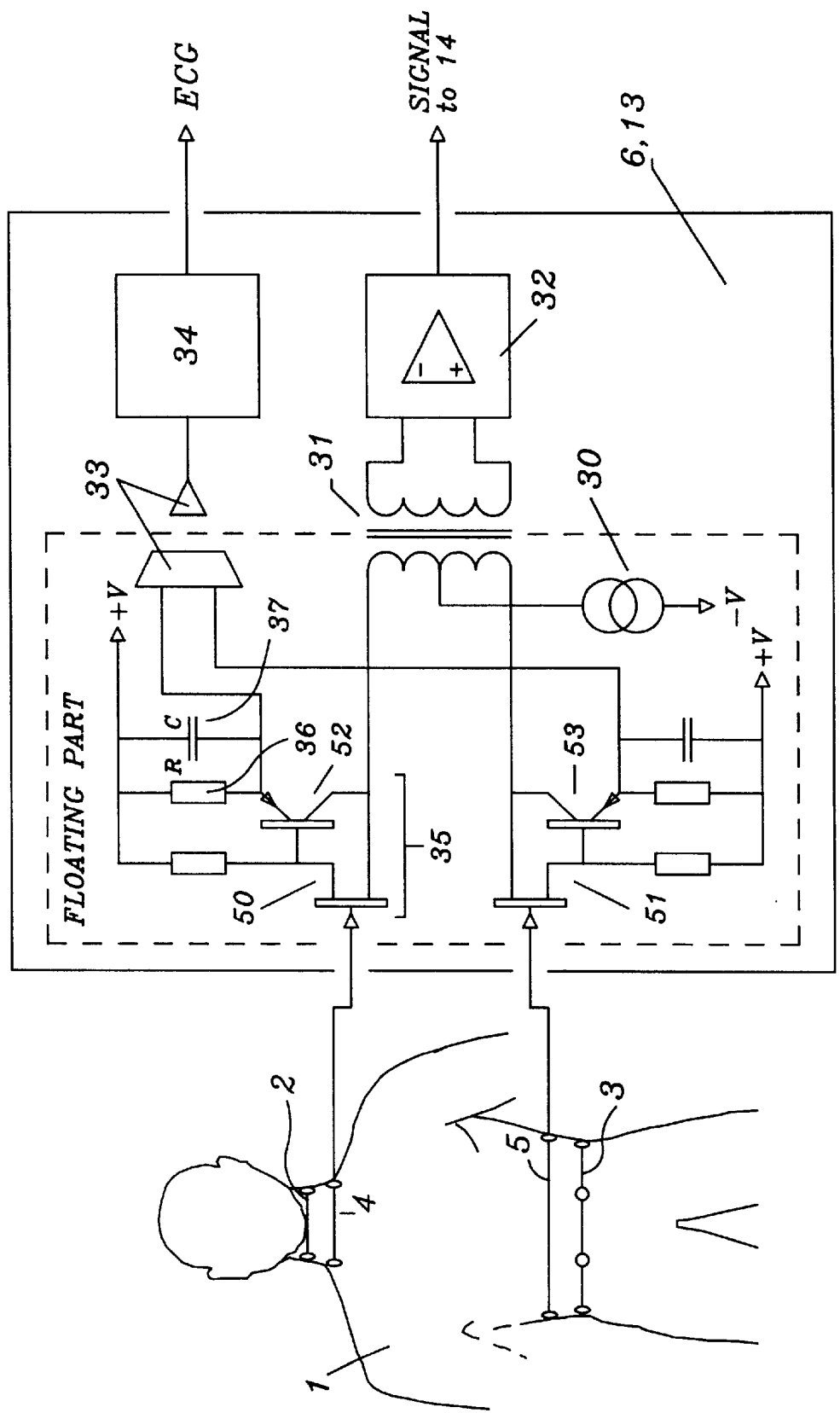
FIG. 4 represents schematically the input stage of the apparatus according to the invention.

FIG. 4 shows a block diagram of the differential amplifiers 6 and 13. Said amplifiers are divided into an electrically insulated part (floating part) comprising a pair of amplifiers 35 consisting of a junction FET 50, 51 and a PNP-transistor 52, 53 arranged symmetrically. The emission resistor 36 and the decoupling capacitor 37 form a time constant τ. The performance of the circuit can be divided into a frequency range below the cut-off frequency $f_c=\frac{1}{2}\pi\tau$ and the frequency range above $f_c$. It may be assumed that below $f_c$ the effect of the transformer 31 becomes negligible as a result of which the circuit behaves like a differential amplifier whose outputs are formed by the emitters of the PNP transistors 52, 53. The signal present on these emitters is passed on via the insulation amplifier 33. For the frequencies well above $f_c$ the circuit behaves like a differencial source follower connected with the transformer 31. In this way the current input side serves as an amplifier for the electrocardiogram signal since this signal holds the frequency to about 100 Hz, being well below $f_c$. Similarly, for frequencies above 1 kHz the circuit serves as input side impedance transformer for the bio-impedance measurement for the conduction of the high frequency signal measured at the location of the electrodes 4 and 5, to transformer 31. Said transformer conducts the signal over the galvanic separation to the amplifier 32 and realizes at the same time an impedance matching. The circuit shown with current source 30 in combination with the floating input, results in suppression of common mode signals at the location of the measuring electrodes.

Figure 5:
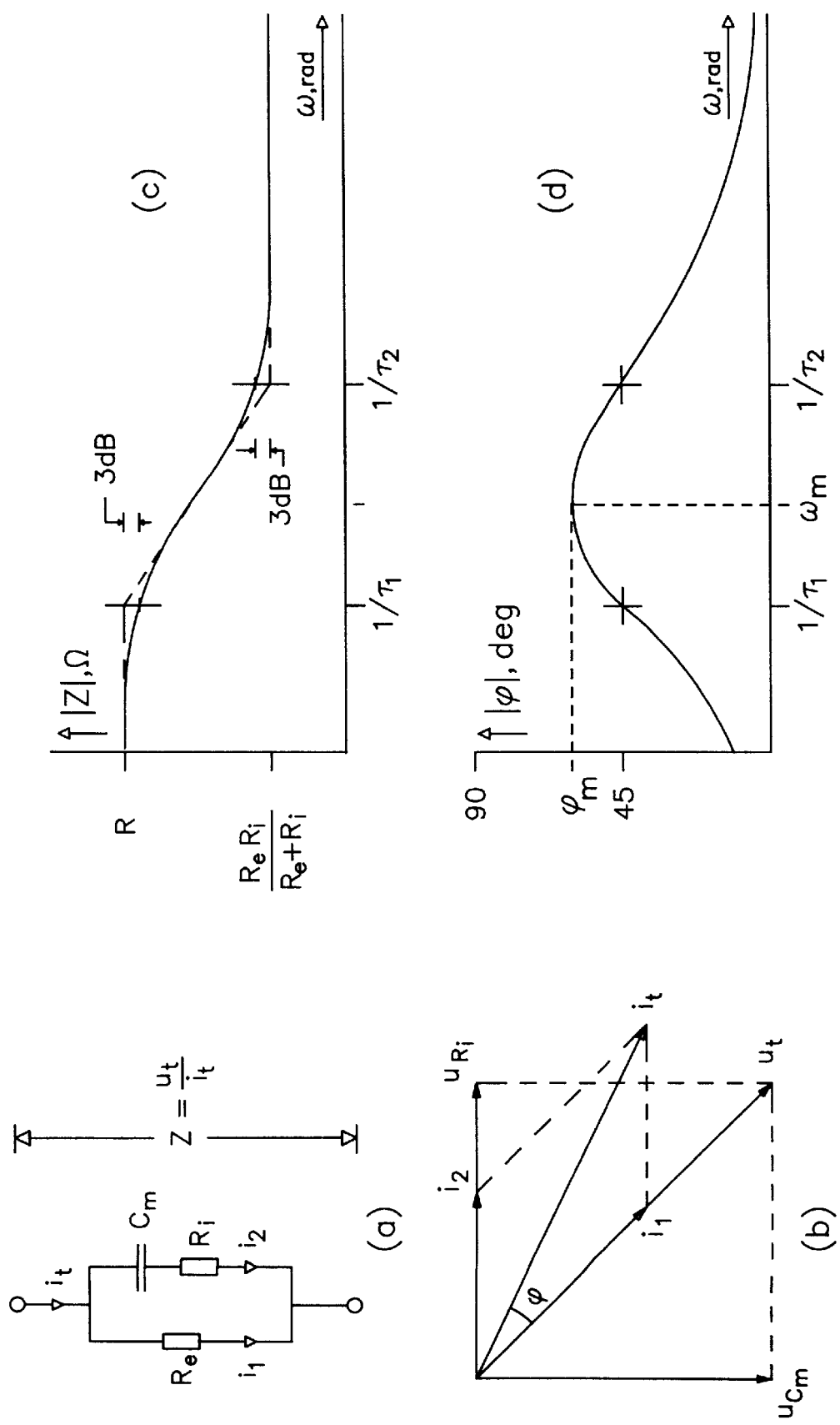
FIG. 5 represents schematically an intra- and extracellular conduction, the so-called Cole-Cole model (5a), with corresponding vector diagram (5b) and Bode plots of amplitude (5c) and phase (5d)

FIG. 5 shows the determination of the frequency behaviour of the Cole-Cole model with the aid of Bode analysis. FIG. 5 shows the actual Cole-Cole model, the vector diagram of current and voltages and the amplitude and phase diagrams as a function of the frequency. The frequency transmission is provided by the formula $$P(j\omega) = \frac{\frac{\tau_2}{\tau_1}\cdot(1+j\omega\tau_1)}{1+j\omega\tau_2} \quad (4)$$

The maximum phase angle $\psi_{max}$ depends on the ratio $\tau_2/\tau_1$ and occurs at frequency $\Omega_m$.

$$\varphi_{max} = 90° - 2\tan^{-1}\sqrt{\frac{\tau_2}{\tau_1}} \quad (5)$$

This results in:

$$\frac{\tau_2}{\tau_1} = \left(\tan\frac{(90°-\varphi_{max})}{2}\right)^2 \quad (6)$$

Since $\tau_1=(R_e+R_i)C_m$ en $\tau_2=R_iC_m$ it follows that:

$$\frac{\tau_2}{\tau_1} = \frac{R_i}{R_e+R_i} \Rightarrow \frac{R_e}{R_i} = \frac{\tau_1}{\tau_2}-1 \quad (7)$$

The equations (5) and (6) can be used for the determination of the intra- and extracellular moisture distribution.

FIG. 6 shows a block diagram of a typical embodiment of the transformers 14 and 15. The signal from the amplifier 32 (see FIG. 4) is fed into a device 40 passing the signal to a demodulator formed by the amplifiers 42, 43 and 44, and a carrier regeneration oscillator 41 based on a phase-locked loop. Said oscillator adapts its frequency dependent on the signal received from device 40 such that no phase shift ensues. The output of oscillator 41 is used for the synchronized connection between the outputs of the amplifiers 42 and 43 in order to obtain complete rectification of the signal at the input of said amplifiers. Further, the output of the oscillator 41 is fed into a phase detector 46 for measuring the phase difference between the signal input of device 40 and a reference signal REF obtained from the optocoupler 28 (see FIG. 3) which depends directly on the current passing through the electrodes 2 and 3. The output of the detector 46 is fed through a low-pass filter 47, which a low-pass filter 47 in itself is known, in order to obtain a signal which is directly related to the phase difference between the current input provided by current source 7, 12 and the voltage measured by means of the differential amplifier 6, 13. The bio-impedance signal Z(t) is obtained by feeding the output from amplifier 44 through a low-pass filter 45, which low-pass filter 45 in itself is known.

The invention has been described in detail with particular emphasis on the preferred embodiment, but variations and modifications within the spirit and scope of the invention may occur to those skilled in the art to which the invention pertains.

What is claimed is:

1. An apparatus for the in-vivo non-invasive measurement of a biological parameter concerning a bodily fluid of a person or animal according to a calculating model, wherein the apparatus is provided with at least two pairs of electrodes adapted to be placed on the skin of a part of the body comprising a pair of input electrodes adapted for feeding a measuring alternating current to the part of the body and a measuring pair of electrodes for measuring the voltage at the electrodes of the measuring pair of electrodes, comprising at least one current source providing the measuring alternating current, a converter for the transformation of the measuring voltage into a bio-impedance signal, being a measure of the bio-impedance of the part of the body, and means for the generation of signals which form a measure for further variables, with the aid of which said parameter can be determined using the calculating model, said signals of said generation of signals encompassing a signal forming a measure for the time derivative of the bio-impedance signal, wherein the at least one current source is electrically symmetrically configured and galvanically separated in relation to ground and is suitable for generating a measuring current having a constant amplitude on at least a low frequency $f_l$, $f_l$ being in the region of about 1–64 kHz, and a high frequency $f_h$, $f_h$ being in the region of about 32–2000 kHz wherein fl is smaller than $f_h$, in a frequency range of up to about 2000 kHz.

2. An apparatus according to claim 1, wherein the parameter is a circulatory parameter of the heart.

3. An apparatus according to claim 1, wherein the parameter is the stroke volume of the heart.

4. An apparatus according to claim 1, wherein the current source is suitable for simultaneous generation of the two frequencies.

5. An apparatus according to claim 1, wherein said apparatus is provided with four pairs of electrodes, two pairs of which serve as an input electrode pair and a measuring electrode pair for taking a transversal bio-impedance measurement at a low and a high frequency and two more pairs which serve as an input electrode pair and a measuring electrode pair for taking a local bio-impedance measurement at a low and a high frequency.

6. An apparatus according to claim 5, wherein said apparatus is provided with connecting means for connecting in series the current source and the transformer, in order to carry out the local bio-impedance measurement and the transversal bio-impedance measurement in sequence.

7. An apparatus according to claim 5, wherein said apparatus comprises a current source or current sources suitable for the simultaneous generation of signals at two low frequencies and two high frequencies.

8. An apparatus according to claim 1, wherein means are provided for the determination of maximum phase shift between the measuring current and the measuring voltage as a function of the frequency.

9. An apparatus according to claim 1, wherein the measurement amplifier for the amplification of the measuring voltage is configured electrically symmetrical and is provided with a galvanic separation in relation to the instrument earth.

10. An apparatus according to claim 9, wherein the measuring amplifier is provided with a galvanic separation which is adapted to be attached to a person.

* * * * *